(12) United States Patent
Hausmann et al.

(10) Patent No.: US 8,219,170 B2
(45) Date of Patent: Jul. 10, 2012

(54) SYSTEM AND METHOD FOR PRACTICING SPECTROPHOTOMETRY USING LIGHT EMITTING NANOSTRUCTURE DEVICES

(75) Inventors: Gilbert Hausmann, Felton, CA (US); Michael P. O'Neil, Pleasanton, CA (US); Paul Mannheimer, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1545 days.

(21) Appl. No.: 11/524,099

(22) Filed: Sep. 20, 2006

(65) Prior Publication Data

US 2008/0071154 A1    Mar. 20, 2008

(51) Int. Cl.
*A61B 5/1455* (2006.01)
(52) U.S. Cl. .................................. 600/323; 600/310
(58) Field of Classification Search ........... 600/309–344
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| 4,281,645 A | 8/1981 | Jobsis |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |

(Continued)

FOREIGN PATENT DOCUMENTS

AU          732799  B2       5/2001

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner* — Eric Winakur
*Assistant Examiner* — Marjan Fardanesh
(74) *Attorney, Agent, or Firm* — Fletcher Yoder

(57) ABSTRACT

Embodiments of the present invention relate to a system and method for practicing spectrophotometry using light emitting nanostructures. Specifically, embodiments of the present invention include a physiologic sensor comprising a sensor body configured for placement adjacent pulsatile tissue of a patient, a first light emitting nanostructure device configured to emit light at a first wavelength through the pulsatile tissue, a second light emitting nanostructure device configured to emit light at a second wavelength through the pulsatile tissue, and a light detector configured to detect the light at the first wavelength and the light at the second wavelength after dispersion through the pulsatile tissue.

23 Claims, 7 Drawing Sheets

U.S. PATENT DOCUMENTS

| | | |
|---|---|---|
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,101,825 A * | 4/1992 | Gravenstein et al. ......... 600/326 |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |

| | | | | | |
|---|---|---|---|---|---|
| 5,368,026 A | 11/1994 | Swedlow et al. | 5,634,459 A | 6/1997 | Gardosi |
| 5,368,224 A | 11/1994 | Richardson et al. | 5,638,593 A | 6/1997 | Gerhardt et al. |
| 5,372,136 A | 12/1994 | Steuer et al. | 5,638,816 A | 6/1997 | Kiani-Azarbayjany et al. |
| 5,377,675 A | 1/1995 | Ruskewicz et al. | 5,638,818 A | 6/1997 | Diab et al. |
| 5,385,143 A | 1/1995 | Aoyagi | 5,645,060 A | 7/1997 | Yorkey et al. |
| 5,387,122 A | 2/1995 | Goldberger et al. | 5,645,440 A | 7/1997 | Tobler et al. |
| 5,390,670 A | 2/1995 | Centa et al. | 5,660,567 A | 8/1997 | Nierlich et al. |
| 5,392,777 A | 2/1995 | Swedlow et al. | 5,662,105 A | 9/1997 | Tien |
| 5,398,680 A | 3/1995 | Polson et al. | 5,662,106 A | 9/1997 | Swedlow et al. |
| 5,402,777 A | 4/1995 | Warring et al. | 5,664,270 A | 9/1997 | Bell et al. |
| 5,402,779 A | 4/1995 | Chen et al. | 5,666,952 A | 9/1997 | Fuse et al. |
| 5,411,023 A | 5/1995 | Morris, Sr. et al. | 5,671,529 A | 9/1997 | Nelson |
| 5,411,024 A | 5/1995 | Thomas et al. | 5,673,692 A | 10/1997 | Schulze et al. |
| 5,413,099 A | 5/1995 | Schmidt et al. | 5,673,693 A | 10/1997 | Solenberger |
| 5,413,100 A | 5/1995 | Barthelemy et al. | 5,676,139 A | 10/1997 | Goldberger et al. |
| 5,413,101 A | 5/1995 | Sugiura | 5,676,141 A | 10/1997 | Hollub |
| 5,413,102 A | 5/1995 | Schmidt et al. | 5,678,544 A | 10/1997 | DeLonzor et al. |
| 5,417,207 A | 5/1995 | Young et al. | 5,680,857 A | 10/1997 | Pelikan et al. |
| 5,421,329 A | 6/1995 | Casciani et al. | 5,685,299 A | 11/1997 | Diab et al. |
| 5,425,360 A | 6/1995 | Nelson | 5,685,301 A | 11/1997 | Klomhaus |
| 5,425,362 A | 6/1995 | Siker et al. | 5,687,719 A | 11/1997 | Sato et al. |
| 5,427,093 A | 6/1995 | Ogawa et al. | 5,687,722 A | 11/1997 | Tien et al. |
| 5,429,128 A | 7/1995 | Cadell et al. | 5,692,503 A | 12/1997 | Kuenstner |
| 5,429,129 A | 7/1995 | Lovejoy et al. | 5,692,505 A | 12/1997 | Fouts |
| 5,431,159 A | 7/1995 | Baker et al. | 5,709,205 A | 1/1998 | Bukta |
| 5,431,170 A | 7/1995 | Mathews | 5,713,355 A | 2/1998 | Richardson et al. |
| 5,437,275 A | 8/1995 | Amundsen et al. | 5,724,967 A | 3/1998 | Venkatachalam |
| 5,438,986 A | 8/1995 | Disch et al. | 5,727,547 A | 3/1998 | Levinson et al. |
| 5,448,991 A | 9/1995 | Polson et al. | 5,730,124 A | 3/1998 | Yamauchi |
| 5,452,717 A | 9/1995 | Branigan et al. | 5,731,582 A | 3/1998 | West |
| 5,465,714 A | 11/1995 | Scheuing | D393,830 S | 4/1998 | Tobler et al. |
| 5,469,845 A | 11/1995 | DeLonzor et al. | 5,743,260 A | 4/1998 | Chung et al. |
| RE35,122 E | 12/1995 | Corenman et al. | 5,743,262 A | 4/1998 | Lepper, Jr. et al. |
| 5,482,034 A | 1/1996 | Lewis et al. | 5,743,263 A | 4/1998 | Baker, Jr. |
| 5,482,036 A | 1/1996 | Diab et al. | 5,746,206 A | 5/1998 | Mannheimer |
| 5,485,847 A | 1/1996 | Baker, Jr. | 5,746,697 A | 5/1998 | Swedlow et al. |
| 5,490,505 A | 2/1996 | Diab et al. | 5,752,914 A | 5/1998 | DeLonzor et al. |
| 5,490,523 A | 2/1996 | Isaacson et al. | 5,755,226 A | 5/1998 | Carim et al. |
| 5,491,299 A | 2/1996 | Naylor et al. | 5,758,644 A | 6/1998 | Diab et al. |
| 5,494,032 A | 2/1996 | Robinson et al. | 5,760,910 A | 6/1998 | Lepper, Jr. et al. |
| 5,494,043 A | 2/1996 | O'Sullivan et al. | 5,766,125 A | 6/1998 | Aoyagi et al. |
| 5,497,771 A | 3/1996 | Rosenheimer | 5,766,127 A | 6/1998 | Pologe et al. |
| 5,499,627 A | 3/1996 | Steuer et al. | 5,769,785 A | 6/1998 | Diab et al. |
| 5,503,148 A | 4/1996 | Pologe et al. | 5,772,587 A | 6/1998 | Gratton et al. |
| 5,505,199 A | 4/1996 | Kim | 5,774,213 A | 6/1998 | Trebino et al. |
| 5,507,286 A | 4/1996 | Solenberger | 5,776,058 A | 7/1998 | Levinson et al. |
| 5,511,546 A | 4/1996 | Hon | 5,776,059 A | 7/1998 | Kaestle |
| 5,517,988 A | 5/1996 | Gerhard | 5,779,630 A | 7/1998 | Fein et al. |
| 5,520,177 A | 5/1996 | Ogawa et al. | 5,779,631 A | 7/1998 | Chance |
| 5,521,851 A | 5/1996 | Wei et al. | 5,782,237 A | 7/1998 | Casciani et al. |
| 5,522,388 A | 6/1996 | Ishikawa et al. | 5,782,756 A | 7/1998 | Mannheimer |
| 5,524,617 A | 6/1996 | Mannheimer | 5,782,757 A | 7/1998 | Diab et al. |
| 5,529,064 A | 6/1996 | Rall et al. | 5,782,758 A | 7/1998 | Ausec et al. |
| 5,533,507 A | 7/1996 | Potratz | 5,786,592 A | 7/1998 | Hök |
| 5,551,423 A | 9/1996 | Sugiura | 5,788,634 A | 8/1998 | Suda et al. |
| 5,551,424 A | 9/1996 | Morrison et al. | 5,790,729 A | 8/1998 | Pologe et al. |
| 5,553,614 A | 9/1996 | Chance | 5,792,052 A | 8/1998 | Isaacson et al. |
| 5,553,615 A | 9/1996 | Carim et al. | 5,795,292 A | 8/1998 | Lewis et al. |
| 5,555,882 A | 9/1996 | Richardson et al. | 5,797,841 A | 8/1998 | DeLonzor et al. |
| 5,558,096 A | 9/1996 | Palatnik | 5,800,348 A | 9/1998 | Kaestle |
| 5,560,355 A | 10/1996 | Merchant et al. | 5,800,349 A | 9/1998 | Isaacson et al. |
| 5,564,417 A | 10/1996 | Chance | 5,803,910 A | 9/1998 | Potratz |
| 5,575,284 A | 11/1996 | Athan et al. | 5,807,246 A | 9/1998 | Sakaguchi et al. |
| 5,575,285 A | 11/1996 | Takanashi et al. | 5,807,247 A | 9/1998 | Merchant et al. |
| 5,577,500 A | 11/1996 | Potratz | 5,807,248 A | 9/1998 | Mills |
| 5,582,169 A | 12/1996 | Oda et al. | 5,810,723 A | 9/1998 | Aldrich |
| 5,584,296 A | 12/1996 | Cui et al. | 5,810,724 A | 9/1998 | Gronvall |
| 5,588,425 A | 12/1996 | Sackner et al. | 5,813,980 A | 9/1998 | Levinson et al. |
| 5,588,427 A | 12/1996 | Tien | 5,817,008 A | 10/1998 | Rafert et al. |
| 5,590,652 A | 1/1997 | Inai | 5,817,009 A | 10/1998 | Rosenheimer et al. |
| 5,595,176 A | 1/1997 | Yamaura | 5,817,010 A | 10/1998 | Hibl |
| 5,596,986 A | 1/1997 | Goldfarb | 5,818,985 A | 10/1998 | Merchant et al. |
| 5,611,337 A | 3/1997 | Bukta | 5,820,550 A | 10/1998 | Polson et al. |
| 5,617,852 A | 4/1997 | MacGregor | 5,823,950 A | 10/1998 | Diab et al. |
| 5,619,992 A | 4/1997 | Guthrie et al. | 5,823,952 A | 10/1998 | Levinson et al. |
| 5,626,140 A | 5/1997 | Feldman et al. | 5,827,179 A | 10/1998 | Lichter et al. |
| 5,630,413 A | 5/1997 | Thomas et al. | 5,827,182 A | 10/1998 | Raley et al. |
| 5,632,272 A | 5/1997 | Diab et al. | 5,829,439 A | 11/1998 | Yokosawa et al. |
| 5,632,273 A | 5/1997 | Suzuki | 5,830,135 A | 11/1998 | Bosque et al. |

| Patent | Date | Name |
|---|---|---|
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,933,791 A * | 8/1999 | Hamada et al. .................. 702/30 |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,990,479 A | 11/1999 | Weiss et al. |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllermann et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schollermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | von der Ruhr et al. |
| 6,321,100 B1 | 11/2001 | Parker |
| 6,330,468 B1 | 12/2001 | Scharf |

| | | |
|---|---|---|
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali |
| 6,381,479 B1 | 4/2002 | Norris |
| 6,381,480 B1 | 4/2002 | Stoddart et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,544,870 B2 * | 4/2003 | Park et al. ............... 438/507 |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,573,991 B1 | 6/2003 | Debreczeny et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,611,320 B1 * | 8/2003 | Lindberg et al. ............... 356/40 |
| 6,615,064 B1 | 9/2003 | Aldrich |
| 6,615,065 B1 | 9/2003 | Barrett et al. |
| 6,618,602 B2 | 9/2003 | Levin et al. |
| 6,618,614 B1 | 9/2003 | Chance |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |

| | | |
|---|---|---|
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-All |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,831,741 B1 | 12/2004 | De Kruif et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,971,580 B2 | 12/2005 | DeLonzor et al. |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,010,341 B2 | 3/2006 | Chance |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,034,071 B2 | 4/2006 | Acquarulo, Jr. et al. |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,107,116 B2 | 9/2006 | Geng |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,984 B1 | 3/2007 | DeLonzor et al. |
| 7,190,986 B1 | 3/2007 | Hannula et al. |
| 7,190,987 B2 | 3/2007 | Lindekugel et al. |
| 7,198,778 B2 | 4/2007 | Achilefu et al. |
| 7,215,984 B2 | 5/2007 | Diab et al. |
| 7,221,969 B2 | 5/2007 | Stoddart et al. |
| 7,225,006 B2 | 5/2007 | Al-Ali et al. |
| 7,228,161 B2 | 6/2007 | Chin |
| 7,236,811 B2 | 6/2007 | Schmitt et al. |
| 7,242,997 B2 | 7/2007 | Geng |
| 7,248,910 B2 | 7/2007 | Li et al. |
| 7,254,433 B2 | 8/2007 | Diab et al. |
| 7,254,434 B2 | 8/2007 | Schulz et al. |
| 7,260,425 B2 | 8/2007 | Chin et al. |
| 7,280,858 B2 | 10/2007 | Al-Ali et al. |
| 7,283,242 B2 | 10/2007 | Thornton |
| 7,289,837 B2 | 10/2007 | Mannheimer et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,319,894 B2 | 1/2008 | Higgins |
| 7,330,746 B2 | 2/2008 | Demuth et al. |
| 7,341,560 B2 | 3/2008 | Henderson et al. |
| 7,349,726 B2 | 3/2008 | Casciani et al. |
| 7,355,688 B2 | 4/2008 | Lash et al. |
| 7,376,451 B2 * | 5/2008 | Mahony et al. ............. 600/310 |
| 7,376,454 B2 | 5/2008 | Casciani et al. |

| | | |
|---|---|---|
| 7,403,804 B2 * | 7/2008 | Ridder et al. .................. 600/310 |
| 7,415,298 B2 | 8/2008 | Casciani et al. |
| 2001/0021803 A1 | 9/2001 | Blank et al. |
| 2001/0051767 A1 | 12/2001 | Williams et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0082489 A1 | 6/2002 | Casciani et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali |
| 2004/0116788 A1 | 6/2004 | Chernoguz et al. |
| 2004/0116789 A1 | 6/2004 | Boas et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167381 A1 | 8/2004 | Lichter |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0215085 A1 | 10/2004 | Schnall |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0014999 A1 | 1/2005 | Rahe-Meyer |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0049470 A1 | 3/2005 | Terry |
| 2005/0049471 A1 | 3/2005 | Aceti |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0195491 A1 * | 9/2005 | Bernard et al. ................ 359/649 |
| 2005/0197548 A1 | 9/2005 | Dietiker |
| 2005/0228248 A1 | 10/2005 | Dietiker |
| 2005/0254992 A1 | 11/2005 | Jenkins et al. |
| 2005/0256386 A1 | 11/2005 | Chan |
| 2005/0267346 A1 | 12/2005 | Faber et al. |
| 2005/0272986 A1 | 12/2005 | Smith |
| 2005/0277819 A1 | 12/2005 | Kiani et al. |
| 2006/0020179 A1 | 1/2006 | Anderson |
| 2006/0025660 A1 | 2/2006 | Swedlow et al. |
| 2006/0030762 A1 | 2/2006 | David et al. |
| 2006/0030763 A1 | 2/2006 | Mannheimer et al. |
| 2006/0030764 A1 | 2/2006 | Porges |
| 2006/0030765 A1 | 2/2006 | Swedlow et al. |
| 2006/0057928 A1 * | 3/2006 | Nagasaka et al. ............... 445/49 |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0155198 A1 | 7/2006 | Schmid |
| 2006/0173257 A1 | 8/2006 | Nagai |
| 2006/0189862 A1 | 8/2006 | Casciani et al. |
| 2006/0195026 A1 | 8/2006 | Casciani et al. |
| 2006/0195027 A1 | 8/2006 | Casciani et al. |
| 2006/0195028 A1 | 8/2006 | Hannula et al. |
| 2006/0211929 A1 | 9/2006 | Casciani et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224058 A1 | 10/2006 | Mannheimer |
| 2006/0229510 A1 | 10/2006 | Fein et al. |
| 2006/0229511 A1 | 10/2006 | Fein et al. |

| | | | | | | |
|---|---|---|---|---|---|---|
| 2006/0264722 | A1 | 11/2006 | Hannula et al. | EP | 630203 | 7/2002 |
| 2006/0264723 | A1 | 11/2006 | Hannula et al. | EP | 01332713 A1 | 8/2003 |
| 2006/0264724 | A1 | 11/2006 | Hannula et al. | EP | 01469773 A1 | 8/2003 |
| 2006/0264725 | A1 | 11/2006 | Hannula et al. | EP | 1502529 | 7/2004 |
| 2006/0264726 | A1 | 11/2006 | Mannheimer et al. | EP | 01491135 A2 | 12/2004 |
| 2006/0264727 | A1 | 11/2006 | Mannheimer et al. | FR | 2685865 | 1/1992 |
| 2006/0276700 | A1 | 12/2006 | O'Neil et al. | GB | 2 259 545 | 3/1993 |
| 2006/0281984 | A1 | 12/2006 | Mannheimer et al. | JP | 63275325 A | 11/1988 |
| 2007/0000531 | A1 | 1/2007 | Russo | JP | 2013450 A | 1/1990 |
| 2007/0015982 | A1 | 1/2007 | Delonzor et al. | JP | 2111343 A | 4/1990 |
| 2007/0021659 | A1 | 1/2007 | DeLonzor et al. | JP | 02 191434 | 7/1990 |
| 2007/0021660 | A1 | 1/2007 | DeLonzor et al. | JP | 2237544 A | 9/1990 |
| 2007/0021661 | A1 | 1/2007 | DeLonzor et al. | JP | 03 173536 | 7/1991 |
| 2007/0021662 | A1 | 1/2007 | DeLonzor et al. | JP | 3170866 A | 7/1991 |
| 2007/0021663 | A1 | 1/2007 | DeLonzor et al. | JP | 3245042 A | 10/1991 |
| 2007/0027377 | A1 | 2/2007 | DeLonzor et al. | JP | 4174648 A | 6/1992 |
| 2007/0027378 | A1 | 2/2007 | DeLonzor et al. | JP | 4191642 A | 7/1992 |
| 2007/0027379 | A1 | 2/2007 | DeLonzor et al. | JP | 4332536 A | 11/1992 |
| 2007/0027380 | A1 | 2/2007 | DeLonzar et al. | JP | 3124073 B | 3/1993 |
| 2007/0032710 | A1 | 2/2007 | Raridan et al. | JP | 5049624 A | 3/1993 |
| 2007/0032712 | A1 | 2/2007 | Raridan et al. | JP | 5049625 A | 3/1993 |
| 2007/0032715 | A1 | 2/2007 | Eghbal et al. | JP | 3115374 B | 4/1993 |
| 2007/0060809 | A1 | 3/2007 | Higgins | JP | 2005/200031 | 8/1993 |
| 2007/0073126 | A1 | 3/2007 | Raridan, Jr. | JP | 5212016 A | 8/1993 |
| 2007/0078307 | A1 | 4/2007 | Debreczeny et al. | JP | 06014906 | 1/1994 |
| 2007/0083094 | A1 | 4/2007 | Colburn et al. | JP | 6016774 B2 | 3/1994 |
| 2007/0114562 | A1 | 5/2007 | Radkov et al. | JP | 3116255 B | 4/1994 |
| 2007/0156039 | A1 | 7/2007 | Casciani et al. | JP | 6029504 U | 4/1994 |
| 2007/0219440 | A1 | 9/2007 | Hannula et al. | JP | 6098881 A | 4/1994 |
| 2007/0235751 | A1 | 10/2007 | Radkov et al. | JP | 06 154177 | 6/1994 |
| 2007/0282178 | A1 | 12/2007 | Scholler et al. | JP | 6269430 A | 9/1994 |
| 2008/0036356 | A1* | 2/2008 | Ward et al. ............... 313/341 | JP | 6285048 A | 10/1994 |
| 2008/0106792 | A1 | 5/2008 | Lash et al. | JP | 7001273 B2 | 1/1995 |
| 2008/0108886 | A1 | 5/2008 | Lash et al. | JP | 7124138 A | 5/1995 |
| 2008/0108887 | A1 | 5/2008 | Higgins | JP | 7136150 A | 5/1995 |
| 2010/0152326 | A1* | 6/2010 | Kurz ............... 523/339 | JP | 3116259 B | 6/1995 |
| | | | | JP | 3116260 B | 6/1995 |
| FOREIGN PATENT DOCUMENTS | | | | JP | 7155311 A | 6/1995 |
| DE | 3405444 | | 8/1985 | JP | 7155313 A | 6/1995 |
| DE | 3516338 | | 11/1986 | JP | 3238813 B2 | 7/1995 |
| DE | 37 03 458 | | 8/1988 | JP | 7171139 A | 7/1995 |
| DE | 3938759 | | 5/1991 | JP | 3134144 B | 9/1995 |
| DE | 4210102 A1 | | 9/1993 | JP | 7236625 A | 9/1995 |
| DE | 4423597 | | 8/1995 | JP | 7246191 A | 9/1995 |
| DE | 19632361 | | 2/1997 | JP | 8256996 A | 10/1996 |
| DE | 69123448 | | 5/1997 | JP | 9192120 A | 7/1997 |
| DE | 19703220 | | 7/1997 | JP | 10216113 A | 8/1998 |
| DE | 19640807 A1 | | 9/1997 | JP | 10216114 A | 8/1998 |
| DE | 19647877 A1 | | 4/1998 | JP | 10216115 A | 8/1998 |
| DE | 10030862 | | 1/2002 | JP | 10337282 A | 12/1998 |
| DE | 20318882 U1 | | 4/2004 | JP | 11019074 A | 1/1999 |
| EP | 0127947 | | 5/1984 | JP | 11155841 A | 6/1999 |
| EP | 00194105 B1 | | 9/1986 | JP | 11 188019 | 7/1999 |
| EP | 00204459 A3 | | 12/1986 | JP | 11244268 A | 9/1999 |
| EP | 0 262 779 | | 4/1988 | JP | 20107157 A | 4/2000 |
| EP | 0315040 | | 10/1988 | JP | 20237170 A | 9/2000 |
| EP | 0314331 | | 5/1989 | JP | 21245871 A | 9/2001 |
| EP | 00352923 A1 | | 1/1990 | JP | 22224088 A | 8/2002 |
| EP | 0 360 977 | | 4/1990 | JP | 22282242 A | 10/2002 |
| EP | 00430340 A3 | | 6/1991 | JP | 23153881 A | 5/2003 |
| EP | 0435 500 | | 7/1991 | JP | 23153882 A | 5/2003 |
| EP | 0572684 | | 5/1992 | JP | 23169791 A | 6/2003 |
| EP | 00497021 A1 | | 8/1992 | JP | 23194714 A | 7/2003 |
| EP | 0529412 | | 8/1992 | JP | 23210438 A | 7/2003 |
| EP | 0531631 | | 9/1992 | JP | 23275192 A | 9/2003 |
| EP | 0566354 | | 4/1993 | JP | 23339678 A | 12/2003 |
| EP | 0587009 | | 8/1993 | JP | 24008572 A | 1/2004 |
| EP | 00630203 B1 | | 9/1993 | JP | 24089546 A | 3/2004 |
| EP | 0 572 684 | | 12/1993 | JP | 24113353 A | 4/2004 |
| EP | 00615723 A1 | | 9/1994 | JP | 24135854 A | 5/2004 |
| EP | 00702931 A1 | | 3/1996 | JP | 24148069 A | 5/2004 |
| EP | 00724860 A1 | | 8/1996 | JP | 24148070 A | 5/2004 |
| EP | 00793942 A3 | | 9/1997 | JP | 24159810 A | 6/2004 |
| EP | 0 864 293 | | 9/1998 | JP | 24166775 A | 6/2004 |
| EP | 01006863 B1 | | 10/1998 | JP | 24194908 A | 7/2004 |
| EP | 01006864 B1 | | 10/1998 | JP | 24202190 A | 7/2004 |
| EP | 0875199 | | 11/1998 | JP | 24248819 A | 9/2004 |
| EP | 00998214 A1 | | 12/1998 | JP | 24248820 A | 9/2004 |
| EP | 0898933 | | 3/1999 | JP | 24261364 A | 9/2004 |

| | | | |
|---|---|---|---|
| JP | 24290412 A | 10/2004 | |
| JP | 24290544 A | 10/2004 | |
| JP | 24290545 A | 10/2004 | |
| JP | 24329406 A | 11/2004 | |
| JP | 24329607 A | 11/2004 | |
| JP | 24329928 A | 11/2004 | |
| JP | 24337605 A | 12/2004 | |
| JP | 24344367 A | 12/2004 | |
| JP | 24351107 A | 12/2004 | |
| JP | 25034472 A | 2/2005 | |
| WO | WO 98/09566 A1 | 10/1989 | |
| WO | WO 90/01293 A1 | 2/1990 | |
| WO | WO 90/04352 | 5/1990 | |
| WO | WO 91/01678 A1 | 2/1991 | |
| WO | WO 91/11137 A1 | 8/1991 | |
| WO | WO 92/00513 | 1/1992 | |
| WO | WO 92/21281 A1 | 12/1992 | |
| WO | WO 93/09711 | 5/1993 | |
| WO | WO 93/13706 A2 | 7/1993 | |
| WO | WO 93/16629 A1 | 9/1993 | |
| WO | WO 94/03102 A1 | 2/1994 | |
| WO | WO 94/23643 A1 | 10/1994 | |
| WO | WO 95/02358 | 1/1995 | |
| WO | WO 95/12349 A1 | 5/1995 | |
| WO | WO 95/16970 | 6/1995 | |
| WO | WO 96/13208 | 5/1996 | |
| WO | WO 96/39927 A1 | 12/1996 | |
| WO | WO 97/36536 | 10/1997 | |
| WO | WO 97/36538 | 10/1997 | |
| WO | WO 97/49330 A1 | 12/1997 | |
| WO | WO 98/17174 A1 | 4/1998 | |
| WO | WO 98/18382 | 5/1998 | |
| WO | WO 98/43071 A1 | 10/1998 | |
| WO | WO 98/51212 A1 | 11/1998 | |
| WO | WO 98/57577 A1 | 12/1998 | |
| WO | WO 99/00053 | 1/1999 | |
| WO | 9929231 A | 6/1999 | |
| WO | WO 99/32030 A1 | 7/1999 | |
| WO | WO 99/47039 A1 | 9/1999 | |
| WO | WO 99/63884 | 12/1999 | |
| WO | WO 00/21438 A1 | 4/2000 | |
| WO | WO 00/28888 A1 | 5/2000 | |
| WO | WO 00/59374 A1 | 10/2000 | |
| WO | 0068692 A | 11/2000 | |
| WO | WO 01/13790 | 3/2001 | |
| WO | WO 01/17421 A1 | 3/2001 | |
| WO | WO 01/47426 | 3/2001 | |
| WO | WO 0116577 | 3/2001 | |
| WO | WO 01/40776 A1 | 6/2001 | |
| WO | WO 01/67946 | 9/2001 | |
| WO | WO 01/76461 A1 | 10/2001 | |
| WO | WO 02/14793 A3 | 2/2002 | |
| WO | WO 02/35999 | 5/2002 | |
| WO | WO 02/062213 | 8/2002 | |
| WO | WO 02/074162 | 9/2002 | |
| WO | WO 02/085202 | 10/2002 | |
| WO | WO 03/000125 A1 | 1/2003 | |
| WO | WO 03/001180 | 1/2003 | |
| WO | WO 03/009750 A3 | 2/2003 | |
| WO | WO 03/011127 A1 | 2/2003 | |
| WO | WO 03/020129 | 3/2003 | |
| WO | WO 03/039326 A3 | 5/2003 | |
| WO | WO 03/063697 | 8/2003 | |
| WO | WO 03/063697 A1 | 8/2003 | |
| WO | WO 03/073924 A1 | 9/2003 | |
| WO | WO 2004/000114 | 12/2003 | |
| WO | WO 2004/006748 A3 | 1/2004 | |
| WO | WO 2004/069046 | 8/2004 | |
| WO | WO 2004/075746 A2 | 9/2004 | |
| WO | WO 2005/002434 | 1/2005 | |
| WO | WO 2005/009221 A2 | 2/2005 | |
| WO | WO 2005/010567 A2 | 2/2005 | |
| WO | WO 2005/010568 A3 | 2/2005 | |
| WO | WO 2005/020120 A2 | 3/2005 | |
| WO | WO 2005/065540 | 7/2005 | |
| WO | 2006047215 A | 5/2006 | |
| WO | WO2006097910 A1 | 9/2006 | |
| WO | WO 2006/104790 | 10/2006 | |
| WO | WO2008020845 A2 | 2/2008 | |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masirno Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; "Multiple diagnosis based on Photoplethysmography: hematocrib, SpO2, pulse and respiration," *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*,' Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

R. Neumann, et al.; "Fourier Artifact suppression Technology Provides Reliable $Sp0_2$," *Abstracts*, A11, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Philipp, Carsten M.; "The future of biophotonics in medicine—A proposal"; Medical Laser Application 21 (2006) 115-122.

PCT Search Report mailed Apr. 2, 2009.

\* cited by examiner

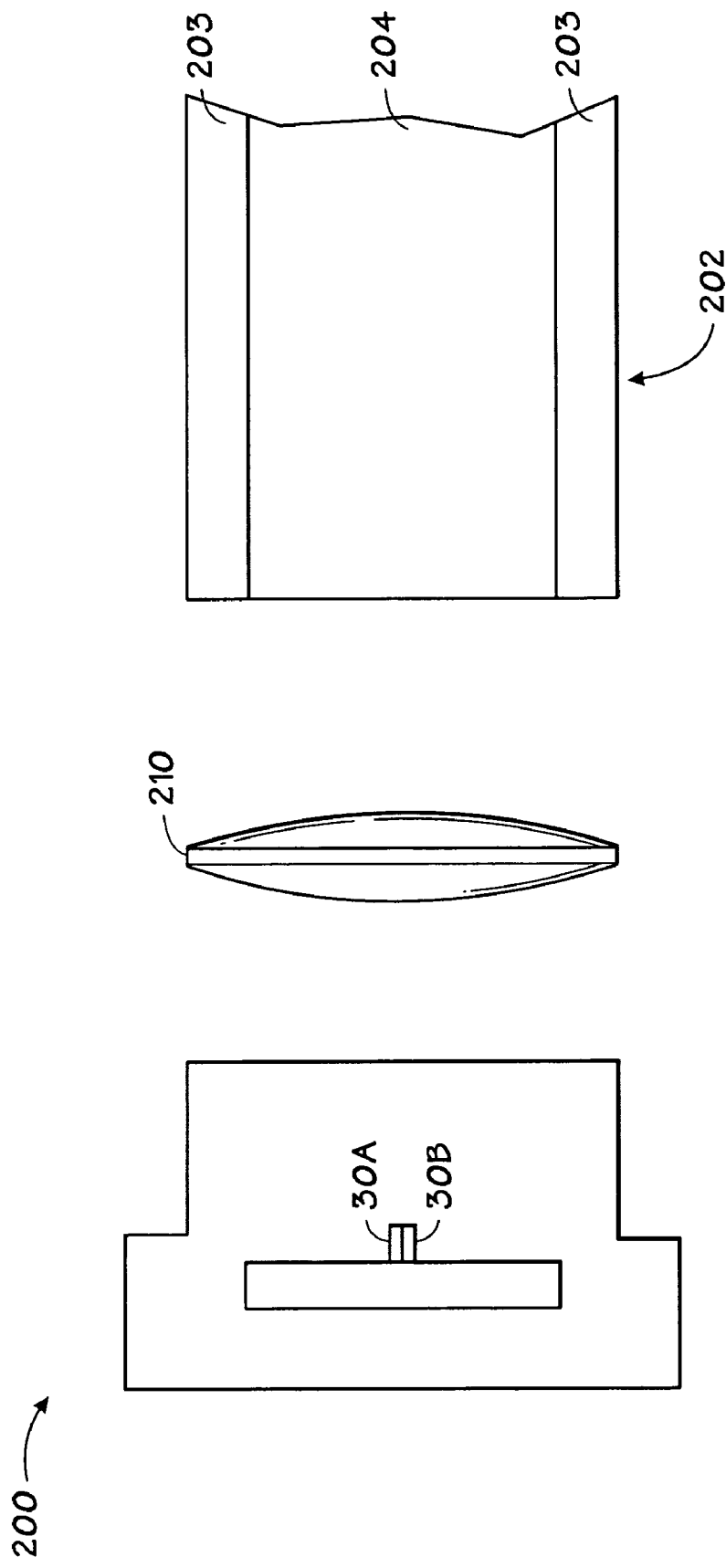

SYSTEM AND METHOD FOR PRACTICING SPECTROPHOTOMETRY USING LIGHT EMITTING NANOSTRUCTURE DEVICES

BACKGROUND OF THE INVENTION

1. Field of the Invention

Embodiments of the present invention relate to spectrophotometry of physiologic tissue, which may include quantitative measurement of reflection or transmission properties of a tissue as a function of wavelength. Specifically, embodiments of the present invention relate to using light emitting nanostructures (LEN), such as light emitting nanotubes, in spectrophotometry.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Spectrophotometry may include the quantitative measurement of the reflection or transmission properties of a material as a function of wavelength. Spectrophotometry of living tissues includes pulse oximetry, which may include non-invasive techniques that facilitate monitoring of a patient's physiological characteristics (e.g., blood flow characteristics). For example, pulse oximetry may be used to measure blood oxygen saturation of hemoglobin in a patient's arterial blood and/or the patient's pulse rate. Specifically, these measurements may be acquired using a non-invasive sensor that passes light through a portion of a patient's blood perfused tissue and photo-electrically senses the absorption and scattering of light through the blood perfused tissue. A typical signal resulting from the sensed light may be translated into what is referred to as a plethysmographic waveform. Once acquired, this measurement of the absorbed and scattered light may be used with various algorithms to estimate an amount of blood constituent in the tissue. It should be noted that the amount of arterial blood in the tissue is time varying during a cardiac cycle, which is reflected in the plethysmographic waveform.

The accuracy of blood flow characteristic estimations obtained via pulse oximetry depends on a number of factors. For example, variations in light absorption characteristics can affect accuracy depending on where (e.g., finger, foot, or ear) the sensor is applied on a patient or depending on the physiology of the patient. Additionally, various types of noise and interference can create inaccuracies. For example, electrical noise, physiological noise, and other artifacts can contribute to inaccurate blood flow characteristic estimates. One source of inaccuracy in measurements obtained by traditional pulse oximeter sensors is inequality between optical pathways from emission to detection points for lights of different wavelengths. Indeed, light emitted from different points may not pass through the same portions of tissue. Such differences in optical pathways make traditional pulse oximeter sensors sensitive to physiological changes, geometrical changes and so forth.

Additionally, traditional pulse oximeter sensors can be inefficient. For example, traditional pulse oximeter sensors often use light emitting diodes (LEDs) that consume a significant amount of power and that produce undesirable heating effects. Indeed, when deep penetration of light into a patient's tissue is desirable to detect certain blood flow characteristics, for example, the increased intensity required of the LEDs may cause discomfort to the patient due to heating. Further, with respect to coupling a sensor to fiber optic cables, traditional pulse oximeter sensors may be inefficient because coupling fiber optics with larger and/or multiple spaced emitters (e.g., LEDs) results in inappropriate matching of fiber diameter and numerical aperture.

Accordingly, it is desirable to provide a system and method that efficiently and conveniently operates to provide accurate and consistent spectrophotometric measurements.

BRIEF DESCRIPTION OF THE DRAWINGS

Advantages of the invention may become apparent upon reading the following detailed description and upon reference to the drawings in which:

FIG. 11 is a block diagram of an emitter coupled with an optical fiber, wherein a lens is incorporated for coupling efficiency in accordance with an exemplary embodiment of the present invention.

DETAILED DESCRIPTION OF SPECIFIC EMBODIMENTS

Figure 1:
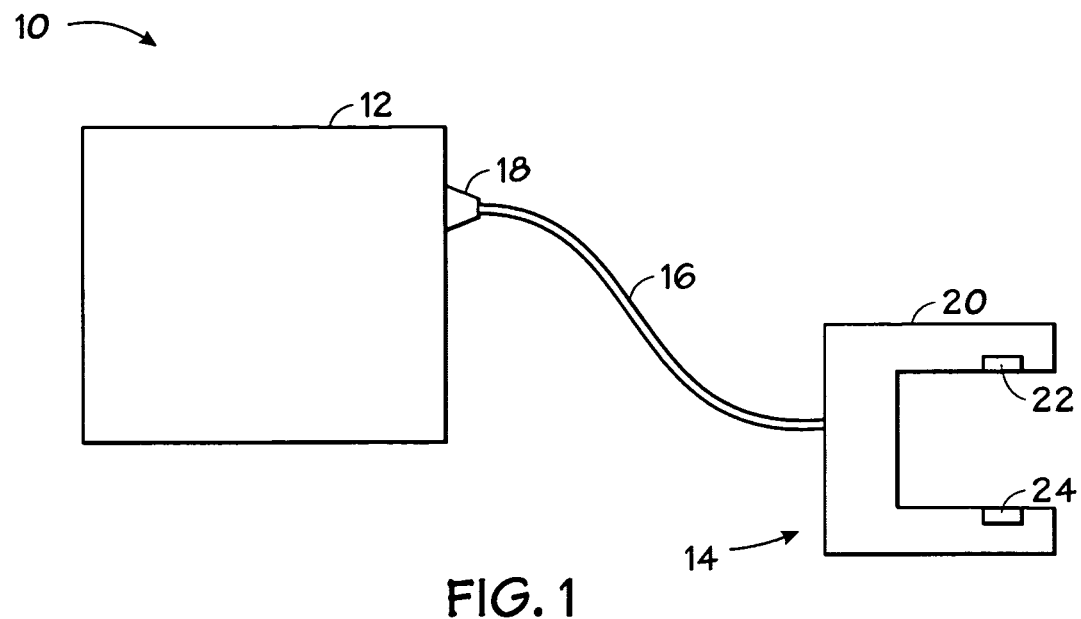
FIG. 1 is a block diagram of a pulse oximeter system in accordance with an exemplary embodiment of the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate to spectrophotometry of a physiologic tissue, which may include quantitative measurement of reflection or transmission properties of a material as a function of wavelength. Specifically, embodiments of the present invention may include using light emitting nanostructure (LEN) devices in spectrophotometry. For example, some embodiments of the present invention are directed to using LEN devices as light emitting devices in pulse oximetry applications, which are included in spectrophotometry. It should be noted that while embodiments of the present invention are described herein as including or utilizing light emitting nanotubes, other embodiments of the present invention may include or utilize other types of nanostructures such as Bucky balls and other quantum restricted elements.

As will be discussed below, certain properties of LEN devices make them desirable for use in sensors (e.g., pulse oximeter sensors) for spectroscopic analysis of tissue or blood constituents. Indeed, LEN-based sensors may improve sensor functionality by consuming less power than traditional LED-based sensors and by providing deeper penetration depth without undesired heating effects. For example, in comparison to the traditionally utilized light emitting diodes (LEDs), LEN devices provide significantly improved efficiencies in creating photons. Such efficiency reduces power requirements and allows for an increase in light penetration depth without undesirable heating effects, which typically accompany such penetration when utilizing LEDs.

In addition to the improvements in efficiency set forth above, the scale and geometry of LEN devices may allow for improved sensor operation based on positioning. For example, the small scale of LEN devices facilitates integration of light emitting devices for multiple light wavelengths on one substrate of sub-millimeter size. In other words, the LEN devices can be essentially co-located. This enables creation of a polychromatic light source that essentially emanates from a single point and facilitates passing multiple wavelengths through the same material (e.g., tissue). Such a "single point" multi-wavelength light source facilitates formation of equal or substantially equal optical pathways from the single emission point to a detection point for light of different wavelengths. Having equal or substantially equal optical pathways for the different light wavelengths makes the sensor less susceptible to measurement discrepancies resulting from physiological or geometrical changes. In other words, more accurate measurement may be facilitated by having a sensor with what amounts to a "single point" multi-wavelength light source.

FIG. 1 is a block diagram of a pulse oximeter system in accordance with an exemplary embodiment of the present invention. The system is generally designated by the reference numeral 10. The system 10 includes a pulse oximeter or monitor 12 that communicatively couples to a sensor 14. The pulse oximeter 12 may be configured to derive patient data (e.g., blood oxygen levels) from signal data detected from a patient and communicated to the pulse oximeter 12 by the sensor 14. The sensor 14 includes a sensor cable 16, a connector plug 18, a body 20 configured to attach to a patient (e.g., patient's finger, ear, forehead, or toe), a light emitting device 22, and a light detector 24. Pulse oximetry systems such as the system 10 may be utilized to observe the oxygenation or oxygen saturation of a patient's arterial blood to estimate the state of oxygen exchange in the patient's body by emitting waves into tissue and detecting the waves after dispersion and/or reflection by the tissue. For example, the pulse oximeter system 10 may emit light from the light emitting device 22 into pulsatile tissue and then detect the transmitted light with the light detector (e.g., a photodiode or photo-detector) 24 after the light has passed through the pulsatile tissue. The amount of transmitted light that passes through the tissue varies in accordance with the changing amount of blood constituent in the tissue and the related light absorption. It should be noted that, in accordance with present embodiments, the light emitting device 22 includes one or more LEN devices configured to emit light of one or more wavelengths.

Figure 2:
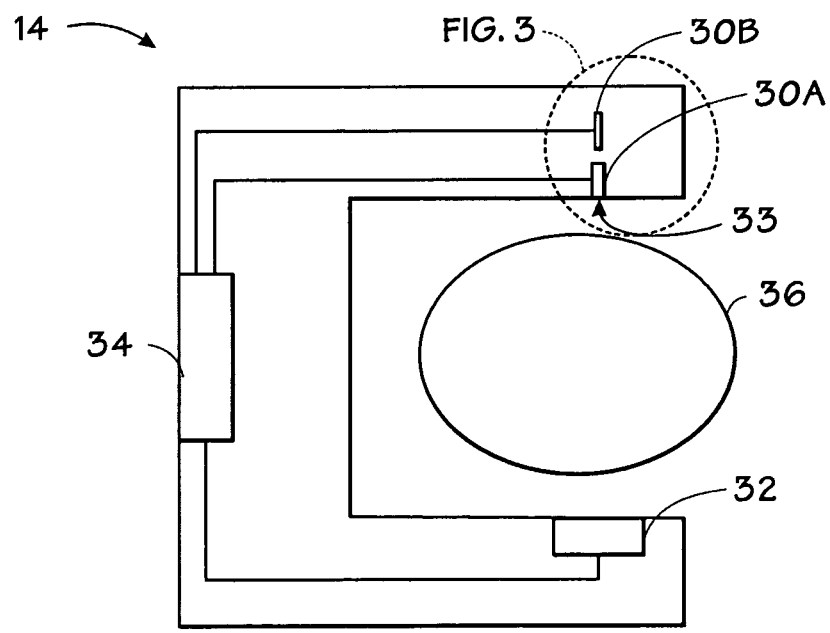
FIG. 2 is a block diagram of a sensor for use in pulse oximetry with two light emitting nanostructure devices aligned to emit light from a single point in accordance with an exemplary embodiment of the present invention.

FIG. 2 is a block diagram of a sensor 14 for use in pulse oximetry in accordance with an exemplary embodiment of the present invention. It should be noted that while FIG. 2 is directed to pulse oximetry, the sensor 14, or similar sensors, may be utilized in different forms of spectrophotometry. Specifically, as illustrated in FIG. 2, sensor 14 includes two LEN devices 30A and 30B and a photo-detector 32. Device 30A may be referred to as an inner LEN device and device 30B may be referred to as an outer LEN device based on their respective relationships to an emission point 33. The illustrated sensor 14 also includes an interface 34 for communicating with the monitor 12. The LEN devices 30A and 30B receive drive signals from the monitor 12 via the interface 34, the drive signals may activate the LEN devices 30A and 30B and cause them to emit signals alternatively. The sensor 14 is configured such that light from the activated LEN devices 30A and 30B can pass into a patient's tissue 36. The light is then dispersed by the tissue and transmitted from or reflected from the tissue 36. The photo-detector 32 receives and/or measures the dispersed light from the tissue 36. Further, in some embodiments, the photo-detector 32 converts the received light into a photocurrent signal, which is then provided to a signal-processing unit (e.g., monitor 12).

To measure the oxygen saturation of the patient's arterial blood, two different wavelengths of light may be emitted from the respective LEN devices 30A and 30B and used to calculate the ratio of oxygenated hemoglobin or oxyhemoglobin ($O_2Hb$) and deoxygenated hemoglobin or deoxyhemoglobin (HHb), which are dominant hemoglobin components. The light passed through the tissue (e.g., tissue 36) may be selected to include two or more wavelengths that are absorbed by the blood in an amount related to the amount of blood constituent present in the blood. Specifically, a first wavelength for one of the LEN devices 30A or 30B may be selected at a point in the electromagnetic spectrum where the absorption of $O_2Hb$ differs from the absorption of HHb. A second wavelength for one of the LEN devices 30A or 30B may be selected at a different point in the spectrum where the absorption of Hhb and $O_2Hb$ differs from those at the first wavelength. For example, wavelength selections for measuring normal blood oxygenation levels typically include a red light emitted at approximately 660 nm and an infrared light emitted at approximately 900 nm.

As set fort above, for pulse oximetry applications, the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra. Spectroscopic measurements of other blood or tissue constituents besides blood oxygen hemoglobin can benefit from the use of LEN devices. For example, measurements related to constituents such as carboxyhemoglobin, methemoglobin, total hemoglobin, bilirubin, glucose, pH, $CO_2$, and so forth.

Figure 3:
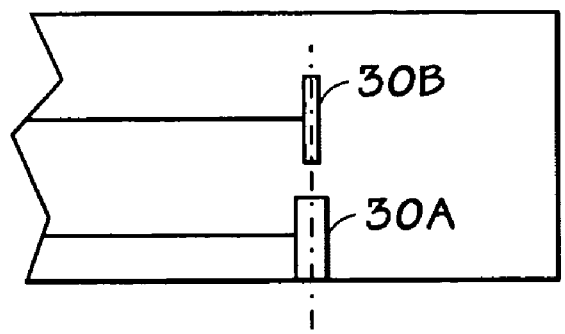
FIG. 3 is a magnified view of the light emitting nanostructure devices illustrated in FIG. 2 in accordance with an exemplary embodiment of the present invention.

Different wavelengths of light may be emitted by the LEN devices 30A and 30B based on physical aspects of the nanostructures. For example, the diameter of an LEN may determine the wavelength of light the LEN emits. Accordingly, wavelengths of emitted light can be controlled by growing the nanostructures (e.g., nanotubes) to have specified diameters. In accordance with present embodiments, various nanostructures may be grown with different diameters to facilitate multi-wavelength light emissions from a single point. For example, as illustrated in FIG. 2, it is believed that the pair of LEN devices 30A and 30B may be formed such that they can be aligned to emit two different wavelengths of light from essentially a single point. In such an embodiment, the diameters of the corresponding nanostructures should be designed to allow wavelengths from the outer LEN device 30B to pass through the inner LEN device 30A. In other words, the diameter of the inner LEN device 30A should accommodate the wavelength of light emitted from the outer LEN device 30B. This may be achieved, for example, by forming the inner LEN device 30A with a larger diameter than the outer LEN device 30B and aligning the LEN devices 30A and 30B along their axes, as illustrated in FIG. 3, which is a magnified view of the LEN devices 30A and 30B in FIG. 2. As set forth above, this may facilitate establishment of equal or substantially equal optical pathways for both wavelengths of light produced by the LEN devices 30A and 30B.

Figure 4:
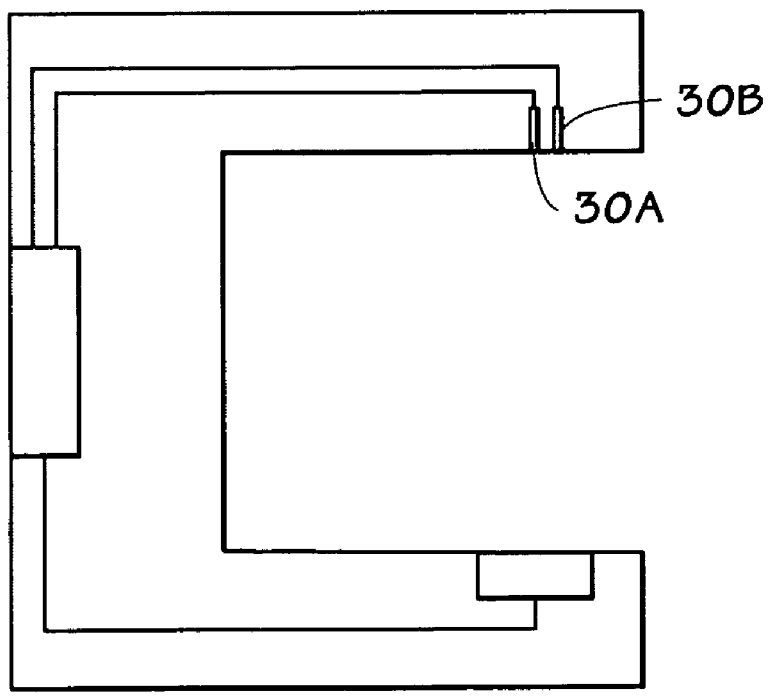
FIG. 4 is a block diagram of a sensor for use in pulse oximetry with light emitting nanostructure devices disposed horizontally adjacent to one another in accordance with an exemplary embodiment of the present invention.
Figure 5:
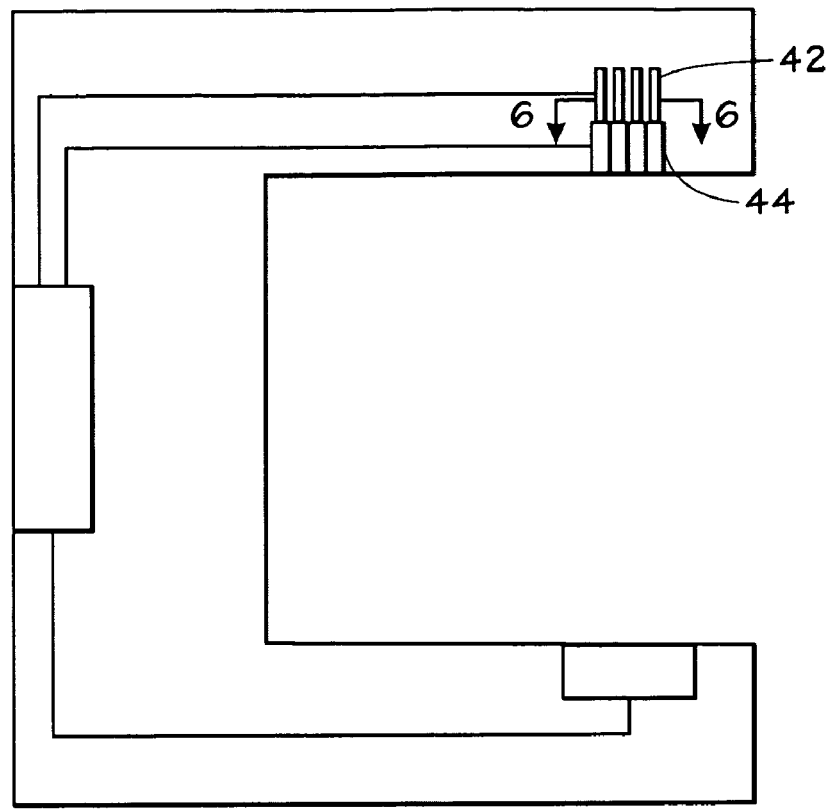
FIG. 5 is a block diagram of a sensor for use in pulse oximetry with stacked and grouped arrays of light emitting nanostructure devices in accordance with an exemplary embodiment of the present invention.
Figure 6:
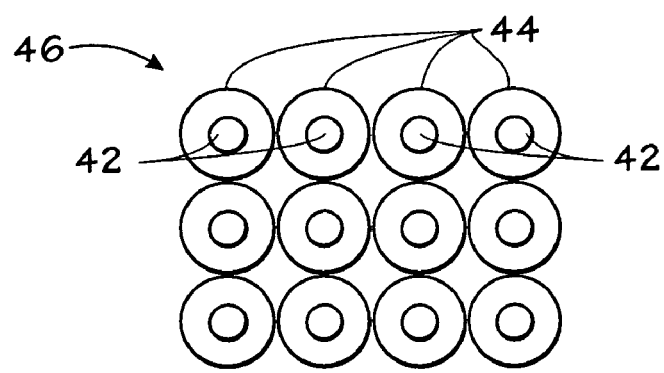
FIG. 6 is a cross-sectional view of an array formed by the light emitting nanostructure devices in FIG. 5 taken along line 6-6, in accordance with an exemplary embodiment of the present invention.

In the embodiment illustrated by FIG. 2, the two LEN devices 30A and 30B are aligned to emit light from essentially a single point. Use of the term single point indicates that the physical separation between the multiple wavelength sources is sufficiently small to have little or no impact on the desired measurement due to geometrical effects. In other embodiments, the LEN devices 30A and 30B may be disposed horizontally adjacent to one another such that light emissions are substantially from the same location, as illustrated in FIG. 4. Further, in some embodiments, a large number of LEN devices designed to emit one or more wavelengths may be grouped together. The LEN devices may be grouped together (e.g., according to diameter) in arrays and/or stacked atop one another, as illustrated in FIG. 5, which includes a first group of devices (e.g., transistors) 42 configured to emit light at a first wavelength and a second group of devices 44 configured to emit light at a second wavelength. FIG. 6 is a cross-sectional view of an array 46 formed by the devices 42 and 44 in FIG. 5. It should be noted that while the array 46 illustrated in FIG. 6 is generally in the shape of a parallelogram, in other embodiments the array 46 may be shaped like an oval, octagon, triangle, and so forth. In some embodiments, the array 46 may be formed such that it improves certain functions of the sensor 14. For example, the array 46 may be shaped to correspond to sensor attachment points (e.g., fingers, ears, toes) to facilitate transmission of light into the attachment points.

Figure 7:
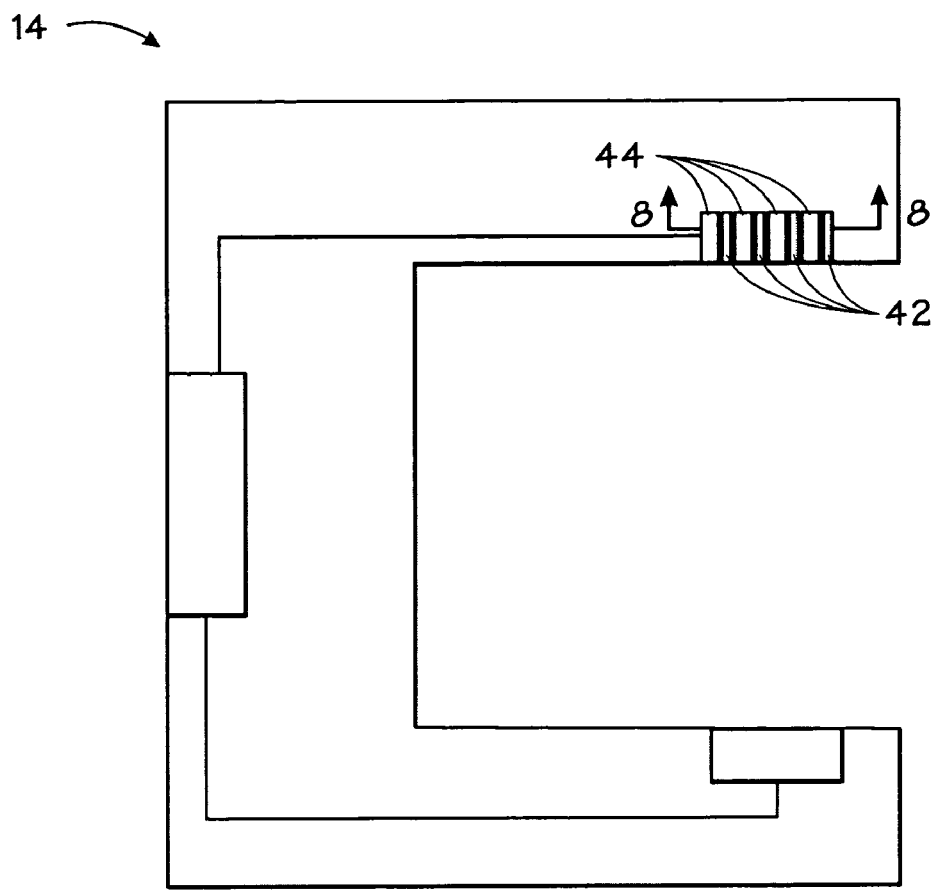
FIG. 7 is a block diagram of a sensor for use in pulse oximetry with light emitting nanostructure devices intermingled and disposed horizontally adjacent to one another in accordance with an exemplary embodiment of the present invention.
Figure 8:
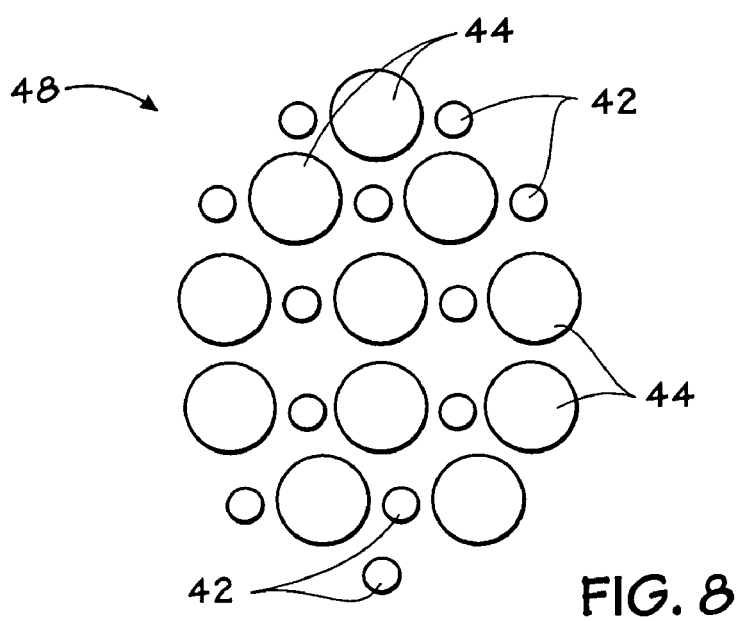
FIG. 8 is a cross-sectional view of an array formed by the light emitting nanostructure devices in FIG. 7 taken along line 8-8, in accordance with an exemplary embodiment of the present invention.

In another embodiment, the first and second groups of LEN devices 42 and 44 may be intermingled and disposed horizontally adjacent to one another in an array to simulate emission from a single point, as illustrated in FIG. 7, wherein the LEN devices may be separated by less than 500 microns or less than 10 microns in some embodiments. For example, by intermingling a number of LEN devices that emit a certain wavelength of light with an equal or approximately equal number of LEN devices that emit a different wavelength of light, embodiments of the present invention may create the effect of two different light wavelength emissions from a single point. FIG. 8 is a cross-sectional view of an array 48 formed by the devices 42 and 44 in FIG. 7. It should be noted that while the array 48 illustrated in FIG. 8 is generally in the shape of an oval, in other embodiments the array 48 may be shaped like a parallelogram, a circle, octagon, triangle, and so forth. In some embodiments, the array 48 may be formed such that it improves certain functions of the sensor 14. For example, the array 48 may be shaped to correspond to sensor attachment points (e.g., fingers, ears, toes) to facilitate transmission of light into the attachment points.

Figure 9:
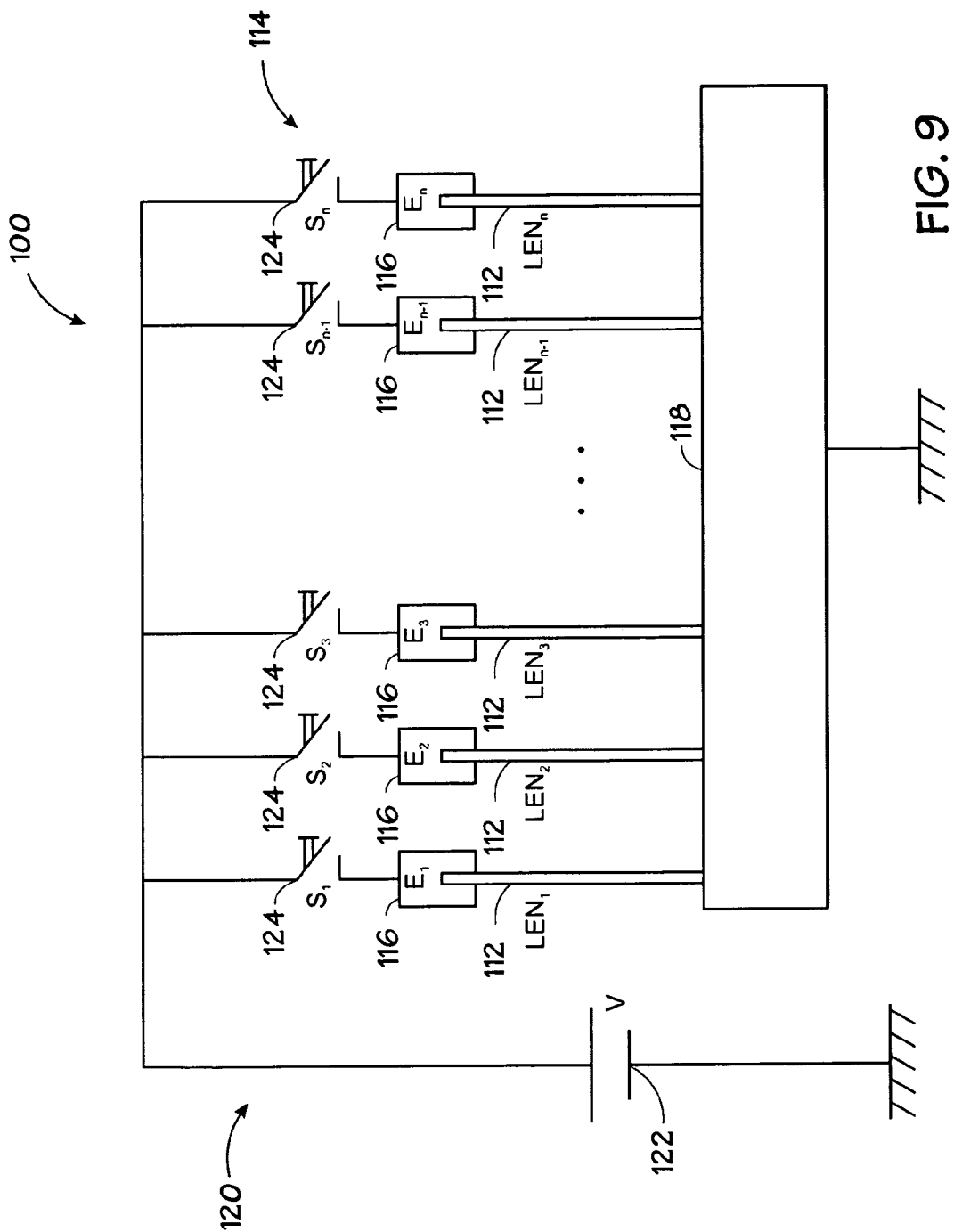
FIG. 9 is a block diagram of a polychromatic point emitting light source using light emitting nanostructures in accordance with an exemplary embodiment of the present invention.

FIG. 9 is a block diagram of a polychromatic point emitting light source using LEN structures in accordance with an exemplary embodiment of the present invention. The light source is generally designated by reference number 100. In the illustrated embodiment, the light source 100 includes multiple LEN structures 112 ($LEN_1$ through $LEN_n$) of different wavelengths that are integrated onto an electrode array 114 with multiple (n) electrodes 116 and a common return 118. An energizing circuit 120 of the light source 100 is symbolically represented as a common source of electricity 122 (V) and multiple switches 124 ($S_1$ through $S_n$). The switches 124 may be implemented using solid state elements such as transistors, which can be integrated onto the same substrate. The switches 124 may be opened and closed in various sequences or in unison to provide desired emission characteristics, e.g., time or frequency multiplexed sequences of two or more wavelengths.

Using energizing circuitry or wiring (e.g., energizing circuit 120) of the light source 100, multiple wavelengths can be simultaneously emitted, individually emitted, or emitted in varying combinations from the various LEN structures 112 over time or frequency as called for by a specific application. For example, the multiple LEN structures 112 of different wavelengths could be individually addressed in sequential order to "sweep" the emission wavelength from one extreme to another (e.g., from 600 nm to 2000 nm). In other words, the switches 124 could be sequentially opened and closed in order based on the value of the wavelength emitted by each of the corresponding LEN structures 112. In another example, the LEN structures 112 may be pseudo-randomly multiplexed by the energizing circuit according to a sequence to enhance the ratio or relationship of accurate electrical signals to unwanted signals (e.g., static disturbances) creating noise. In yet another embodiment, the light source 100 may be configured to emit groups of wavelengths to achieve a desired color (as seen by the human eye) using a one or two-dimensional array of such emitters (e.g., the arrays of FIGS. 6 and 8) configured to create a flat-panel type displayed image, as achieved using liquid crystal displays (LCDs) or plasma cells.

In one embodiment, the multiple LEN structures 112 may be employed as a full spectrum or semi-full spectrum spectrometer. In other words, the multiple LEN structures 112 may emit a range of light wavelengths in a full spectrum or semi-full spectrum (e.g., 600 nm to 700 nm) to facilitate detection of various constituents in material (e.g., blood, water, cerebral-spinal fluid) being monitored. For example, emitting a range of light wavelengths in a full spectrum may facilitate detection of a large number of different types of constituents, each of which may absorb a different light wavelength. By emitting light wavelengths over a range, information may be obtained at and around certain critical wavelengths that have been found to correspond to particular constituents of interest (e.g., lipids, sterols, hemoglobin). Thus, detection of the presence, absence, and/or amount of such constituents of interest may be facilitated. For example, data obtained from emitting a range of wavelengths may be utilized to establish graphical data (e.g., curves), which can be integrated to determine certain characteristics of the material being monitored. In a specific example, the area under a curve around a particular critical wavelength may be correlated to empirical data that suggests how much of a particular constituent is present in the monitored material.

Embodiments of the present invention may facilitate a range of light emissions in a full spectrum or semi-full spectrum because the LEN structures 112 are small compared to LEDs, which allows for emission from what is essentially a single emission point. Further, the LEN structures 112 may prevent heating effects typically associated with light emissions over a range of a full or semi-full spectrum. It should be noted that a semi-full spectrum may be defined to correspond to a particular material being analyzed. For example, most constituents of interest in blood may be detected in a range from 600 nm to 700 nm. Limiting light emissions to a semi-full spectrum may be beneficial in that it may limit the number of LEN structures 112.

Figure 10:
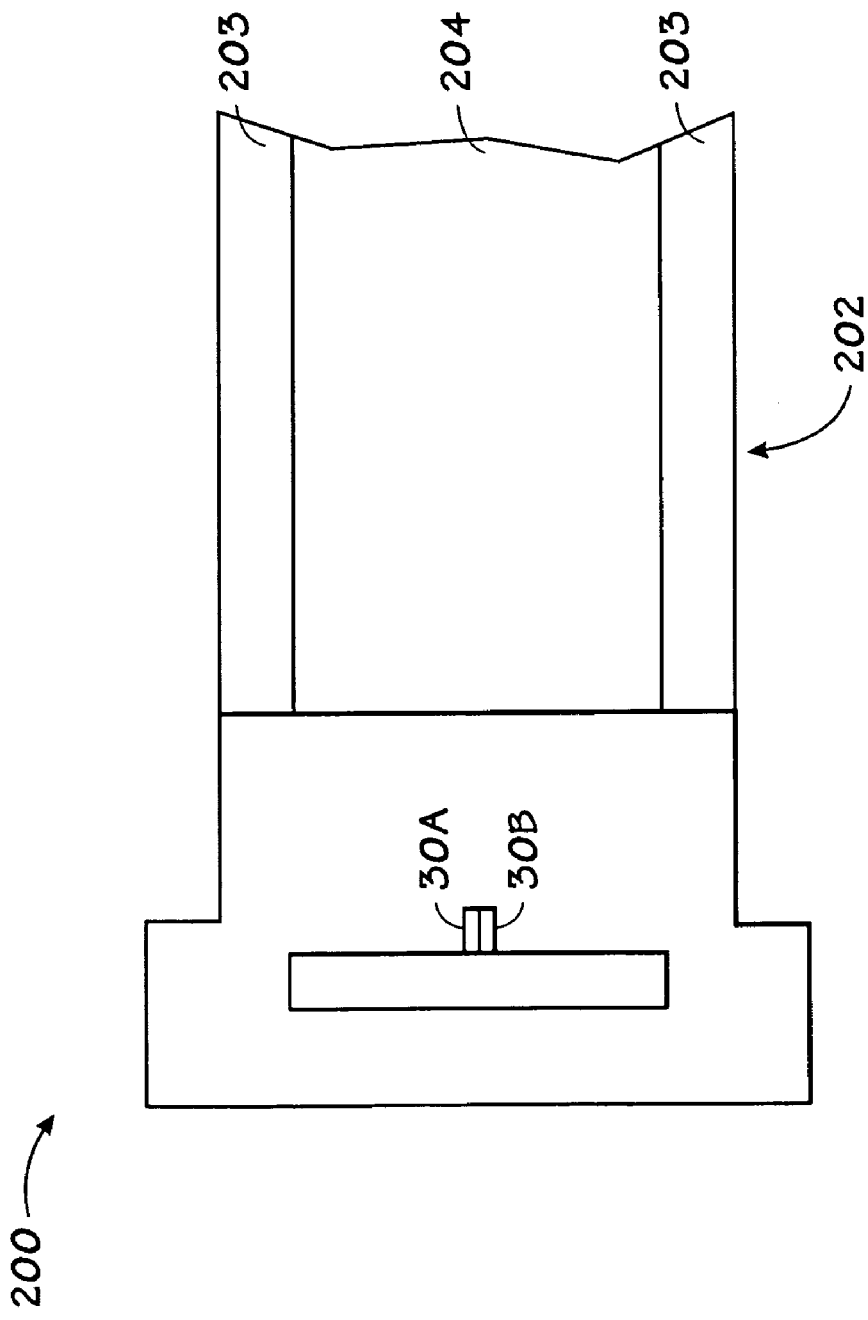
FIG. 10 is a bock diagram of an emitter coupled with an optical fiber in accordance with an exemplary embodiment of the present invention.

FIG. 10 is a block diagram of an emitter 200 coupled with optical fiber 202 in accordance with an exemplary embodiment of the present invention. It is often desirable to utilize fiber optics in spectrophotometry. Fiber optics allow sensor elements (e.g., detectors and emitters) to be located remotely from the patient. For example, fiber optics may be used in pulse oximetry when measuring blood flow characteristics in a patient during magnetic resonance imaging (MRI) procedures to avoid the use of certain materials (e.g., metal) in the MRI machine. Small light emitting devices, such as the LEN devices described herein, facilitate efficient transmission of light with multiple wavelengths from the emitter 200 into optical fiber 202, that is comprised of a cladding 203 and core 204. Because the dimensions of the LEN devices 30A and 30B are small compared to traditional light emitting devices, such as LEDs, a multi-wavelength source area can be provided that is smaller than the diameter of the optical fiber core 204. Thus, the multiple wavelengths of light can be readily lensed to match the fiber diameter and numerical aperture. In other words, light can be more efficiently directed into fiber optics utilizing LEN devices 30A and 30B in accordance with present embodiments. As illustrated in FIG. 11 and as understood by those skilled in the art, the use of lensing components, such as lens 210, can further improve coupling efficiency, as enabled by the small size of the source.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A physiologic sensor, comprising:
a sensor body configured for placement adjacent tissue of a patient;
a first light emitting nanostructure device configured to emit light at a first wavelength into the tissue;
a second light emitting nanostructure device configured to emit light at a second wavelength into the tissue, wherein the first and second light emitting nanostructure devices are stacked atop one another to substantially align an axis of emission of the first light emitting nanostructure device with an axis of emission of the second light emitting nanostructure device; and
a light detector configured to detect the light at the first wavelength and the light at the second wavelength from the tissue.

2. The physiologic sensor of claim 1, wherein the first wavelength is at a point in the electromagnetic spectrum where absorption by oxyhemoglobin differs from absorption by deoxyhemoglobin.

3. The physiologic sensor of claim 2, wherein the second wavelength is at a point in the electromagnetic spectrum where absorption by oxyhemoglobin and the absorption by deoxyhemoglobin are different than the first wavelength.

4. The physiologic sensor of claim 1, comprising a plurality of light emitting nanotube devices arranged in a matrix, wherein the plurality of light emitting nanotube devices comprise the first and second light emitting nanostructure devices.

5. The physiologic sensor of claim 4, wherein approximately half of the plurality of light emitting nanotube devices are configured to emit light at the first wavelength through the pulsatile tissue and the remaining light emitting nanotube devices are configured to emit light at the second wavelength.

6. The physiologic sensor of claim 1, wherein the first light emitting nanostructure device is configured to emit a red light at approximately 660 nm.

7. The physiologic sensor of claim 1, wherein the first light emitting nanostructure device is configured to emit an infrared light at approximately 900 nm.

8. The physiologic sensor of claim 1, wherein the first and second light emitting nanostructure devices comprise nanotubes.

9. The physiologic sensor of claim 8, wherein the first light emitting nanostructure device is arranged within the sensor body for placement adjacent the pulsatile tissue and has a diameter sufficient to accommodate light emitted from the second light emitting nanostructure device.

10. The physiologic sensor of claim 1, comprising a plurality of light emitting nanostructure devices arranged in a matrix having a substantially oval shape.

11. The physiologic sensor of claim 1, comprising a plurality of light emitting nanostructure devices arranged in a matrix having a substantially parallelogram shape.

12. The physiologic sensor of claim 1, comprising a plurality of light emitting nanostructure devices arranged in a matrix, wherein a first group of the plurality of light emitting nanostructure devices is stacked adjacent a second group of the plurality of light emitting nanostructure devices, wherein the first and second group emit light in the same direction.

13. The physiologic sensor of claim 12, wherein an axis of emission of each of the nanostructure devices in the first group are aligned with an axis of emission of each of the nanostructure devices in the second group.

14. A pulse oximeter system, comprising:
a pulse oximeter configured to read signal data and derive patient data from the signal data; and
a sensor configured to detect physiological characteristics of a patient and communicate the physiological characteristics to the pulse oximeter as the signal data, comprising:
a sensor body configured for placement adjacent pulsatile tissue of the patient;

a first light emitting nanostructure device configured to emit light at a first wavelength into the pulsatile tissue;

a second light emitting nanostructure device configured to emit light at a second wavelength into the pulsatile tissue, wherein the first and second light emitting nanostructure devices are stacked atop one another to substantially align an axis of emission of the first light emitting nanostructure device with an axis of emission of the second light emitting nanostructure device; and a light detector configured to detect the light at the first wavelength and the light at the second wavelength from the pulsatile tissue.

15. The pulse oximeter system of claim 14, comprising a plurality of light emitting nanotube devices arranged in a matrix, wherein the plurality of light emitting nanotube devices comprise the first and second light emitting nanostructure devices.

16. The pulse oximeter system of claim 15, wherein approximately half of the plurality of light emitting nanotube devices are configured to emit light at the first wavelength through the pulsatile tissue and the remaining light emitting nanotube devices are configured to emit light at the second wavelength.

17. The pulse oximeter system of claim 14, wherein the first and second light emitting nanostructure devices comprise nanotubes.

18. The pulse oximeter sensor of claim 17, wherein the first light emitting nanostructure device is arranged within the sensor body for placement adjacent the pulsatile tissue and has a diameter sufficient to accommodate light emitted from the second light emitting nanostructure device.

19. A method, comprising:

providing a sensor body configured for placement adjacent tissue of a patient;

disposing a first light emitting nanostructure device in the sensor body, the first light emitting nanostructure device configured to emit light at a first wavelength into the tissue;

disposing a second light emitting nanostructure device in the sensor body, the second light emitting nanostructure device configured to emit light at a second wavelength into the tissue, wherein the first and second light emitting nanostructure devices are stacked atop one another to substantially align an axis of emission of the first light emitting nanostructure device with an axis of emission of the second light emitting nanostructure device; and providing a light detector configured to detect the light at the first wavelength and the light at the second wavelength from the tissue.

20. The method of claim 19, wherein the first and second light emitting nanostructures are nanotubes.

21. The method of claim 19, comprising disposing an array of a plurality of light emitting nanotubes in the sensor body.

22. A method of determining a blood flow characteristic in a patient, comprising:

emitting light at a first wavelength from a first light emitting nanostructure device into tissue;

emitting light at a second wavelength from a second light emitting nanostructure device into the tissue, wherein the first and second light emitting nanostructure devices are stacked atop one another to substantially align an axis of emission of the first light emitting nanostructure device with an axis of emission of the second light emitting nanostructure device;

detecting the light from the tissue; and calculating a blood flow characteristic based on the detected light.

23. The method of claim 22, comprising emitting the second light through the first light emitting nanostructure.

* * * * *